United States Patent [19]

Schoendorfer et al.

[11] 4,425,114
[45] Jan. 10, 1984

[54] BLOOD DONATION UNIT

[75] Inventors: Donald W. Schoendorfer, Brookline; Richard M. Lueptow, Quincy; Jonathan D. Schiff, Boston, all of Mass.

[73] Assignee: Haemonetics Corporation, Braintree, Mass.

[21] Appl. No.: 256,694

[22] Filed: Apr. 23, 1981

[51] Int. Cl.³ .............................................. A61M 5/00
[52] U.S. Cl. ........................................ 604/7; 604/416
[58] Field of Search ............ 128/276, 277, 278, 214 F, 128/214 B, 214 R, 240, DIG. 12, DIG. 19; 222/95, 97, 389; 604/7-9, 403, 406, 408, 416

[56] References Cited

U.S. PATENT DOCUMENTS

| | | | |
|---|---|---|---|
| 2,074,223 | 3/1937 | Horiuchi | 128/DIG. 12 |
| 2,406,207 | 8/1946 | Desmet | 128/214 |
| 2,982,286 | 5/1961 | Welch, Jr. | 128/276 |
| 2,999,500 | 9/1961 | Schurer | 128/276 |
| 3,032,037 | 5/1962 | Huber | 128/276 |
| 3,153,414 | 10/1964 | Beall et al. | 128/214 |
| 3,640,277 | 2/1972 | Adelberg | 128/214 F |
| 3,896,803 | 7/1975 | Mason | 128/214 |
| 3,916,892 | 11/1975 | Latham, Jr. | 128/240 |
| 4,033,479 | 7/1977 | Fletcher et al. | 128/214 F |
| 4,086,924 | 5/1978 | Latham, Jr. | 128/214 R |
| 4,090,514 | 5/1978 | Hinck et al. | 128/DIG. 12 |
| 4,146,172 | 3/1979 | Cullis et al. | 233/26 |
| 4,195,631 | 4/1980 | Baucom | 128/214 |
| 4,335,835 | 6/1982 | Beigler et al. | 222/95 |
| 4,337,769 | 7/1982 | Olson | 128/DIG. 12 |

OTHER PUBLICATIONS

"SRR Lab Introduces New Blood Collection Technology", 10/79.

Primary Examiner—C. Fred Rosenbaum
Assistant Examiner—J. L. Kruter
Attorney, Agent, or Firm—Hamilton, Brook, Smith & Reynolds

[57] ABSTRACT

A blood donation unit in which a phlebotomy needle is coupled on one conduit to a source of anticoagulant contained in a flexible bag and on another conduit to a flexible collection bag. The anticoagulant bag and collection bag are placed in a chamber within which a vacuum is created, preferably by a hand pump operated by the donor. A rigid plate is disposed between the two bags. The blood flow from the donor is maintained at an adaquate flow level by the donor's pumping which provides a pressure differential between the bags and the needle. The whole blood is mixed with anticoagulant immediately after passing through the phlebotomy needle. The ratio of whole blood to anticoagulant is independent of the volume of whole blood collected and is fixed by the ratio of the surface areas of opposing bag surfaces at the interface with the plate.

22 Claims, 16 Drawing Figures

BLOOD DONATION UNIT

DESCRIPTION

Technical Field

This invention is in the field of blood donation apparatus.

Background Art

In the collection of blood, and more particularly human blood, it is desired that the blood be collected at a controlled rate, such rate to afford minimal physiologic disturbance to the donor and which will preclude damage to the blood cells which would be caused by shearing forces in the event the flow exceeds a certain level. It is also desirable to obtain and store the blood in predetermined volumes and that the collected blood be promptly and completely mixed with anticoagulant solution at specified ratios of blood to anticoagulant so as to minimize damage to the blood.

Conventional systems for collecting blood rely on venous pressure, and hydrostatic pressure to cause blood to flow from a donor's arm. Venous pressure is controllable to some extent by varying the pressure in the cuff attached to the donor's arm above the venipuncture site and by directing the donor to alternately flex and relax his or her hand. Hydrostatic pressure is achieved by positioning the collection bag below the level of the donor's arm, usually about 18" below. This produces a hydrostatic head of about 34 torr.

In U.S. Pat. No. 2,982,286 to E. S. Welch, Jr., issued on May 2, 1961, there is disclosed a so-called "hemolater" which adds a third controllable source of pressure differential.

The "hemolator" consists of a 500 cc flexible plastic bag which is supplied with 75 cc of anticoagulant. The bag is placed in a rigid chamber. A vacuum on the inside of the chamber and the outside of the bag is created by a vacuum pump causing a negative pressure inside the bag. Blood flows from a donor's vein, which is under a slight positive pressure due to a pressure cuff, through a needle and tube to the bag which is under controlled negative pressure. Means are supplied for agitating the bag while the blood is being drawn and means are also supplied for automatically detecting and measuring the presence of a desired amount of fluid volume in the bag. The rate of flow of blood into the bag is determined by adjustment of a vacuum regulator valve. During the collection of blood, the chamber is continuously pumped and maintained at a level of vacuum as determined by the setting of a screw on the vacuum regulator valve.

In practice, this system has several deficiencies, the most important one being that the flow of blood from the donor is primarily determined by the vacuum set by the set screw in the vacuum regulator valve. The customary 16 gauge size phlebotomy needles were used in this system, and the vacuum regulator could be mistakenly set to produce a vacuum high enough to produce rapid blood flow from the donor which would lead to physiological shock conditions.

With the exception of the "hemolator" as above described, it has become customary within the industry to rely solely on the venous pressure and hydrostatic pressure to determine the rate of flow from the donor. It is also customary to utilize a size 16 gauge needle because it is easy to achieve good flow rates with this size needle utilizing solely venous pressure and hydrostatic pressure. However, the 16 gauge needle which has a 0.065 inch outer diameter is a significant deterrent to donor recruitment, due to the pain associated with the venipuncture.

Many of the problems associated with this common technique of whole blood collection stem from the fact that the non-anticoagulated whole blood must pass through the phlebotomy needle and at least 30 inches of tubing before it reaches the anticoagulant in the blood collection bag. If the rate of flow of blood is not maintained at a rapid enough level in the 30 inch section of tubing the activation of clotting factors may occur. When this happens, the clinical usefulness of the blood collection is greatly diminished.

Other problems with the prior art technique are associated with the way the whole blood and the anticoagulant are combined. The amount of anticoagulant which is included in the collection bag is predetermined so that the ratio of final volume of whole blood to anticoagulant is controlled (for example, 7 parts whole blood to one part CPD anticoagulant). However, the first volume of blood that enters the collection bag sees a much greater anticoagulant to whole blood ratio. There is evidence that this transient inflated anticoagulant to whole blood ratio will adversely affect many of the blood components such as Factor VIII and platelet viability. This prior art technique of whole blood collection also requires accurate control of the volume of whole blood collected so that the final whole blood to anticoagulant ratio will be within clinical specifications. This results in a significant wastage of blood due to units of blood that are "overdrawn" or "underdrawn" with respect to the whole blood/anticoagulant ratio.

The American Association of Blood Bank (AABB) publishes guidelines in its Technical Manual (7th Edition) which result in a fairly large percentage of:

(a) rejected drawn units of whole blood for specific clinical applications because a specific volume of whole blood (405 to 495 milliliters) was not collected in less than a specific amount of time (8 minutes);

(b) rejected donors, either because they are less than 110 pounds and cannot donate a full unit of blood or because their previous donation experiences have resulted in rejected units. Donors weighing less than 110 pounds may only donate if provisions are available for manually reducing the amount of anticoagulant in the collection bag so that less whole blood can be collected.

The AABB also recommends that the blood collection bag be agitated during the collection process as often as every 50 milliliters (ml) of collected blood to insure proper anticoagulant mixing.

The cause for rejection of the above mentioned drawn units of whole blood and potential donors is believed to be inherent in the prior art technique of blood collection.

One solution for this problem has been proposed in copending U.S. patent application Ser. No. 182510 filed Aug. 29, 1980 to Gilcher et al. In the Gilcher et al. system, whole blood is withdrawn from a donor using a needle which is between 30%–50% smaller than the outside diameter of the customary size 16 gauge needle. Anticoagulant is introduced and mixed with the whole blood at the outlet of the phlebotomy needle from a tube which is connected to a source of anticoagulant. The anticoagulant tube is passed through a roller pump. The rollers of the pump are in resilient contact with both the outer surface of the anticoagulant tubing and the outer surface of the tubing which serves as a conduit for the anticoagulated blood. Thus, the same pump which controls the flow of the anticoagulant also controls the flow of blood from the donor thereby assuring an accurate ratio of blood to anticoagulant, the ratio being determined by the ratio of the pump tube dimensions and elastic characteristics.

While the Gilcher et al. system is a significant improvement over prior art systems, certain disadvantages still exist in the Gilcher et al. system for particular applications. For example, it is sometimes advantageous to obtain blood donations in remote areas where electrical power to operate the roller pump used in the Gilcher et al. system would be unavailable. Also, in the Gilcher et al. system, the dimensions of the blood tubing are relatively critical, in that it is important that the diameter of the tubing, especially at the roller pump, be precisely fixed for mixing of anticoagulant and whole blood in correct ratios.

In addition, in all known prior art systems, the flow of whole blood is not in the control of the donor but depends either on hydrostatic or venous pressure or mechanical pressure means uncontrolled by the donor.

Accordingly, a need exists for a simple, inexpensive method and mechanism for drawing blood from donors which may be controlled by the donor and requires no other source of energy for motive power and in which the ratio of whole blood collected to anticoagulant mixed is fixed and continuously controlled.

DISCLOSURE OF THE INVENTION

In a preferred embodiment of the apparatus of the present invention, a hand operated pump is used to create a pressure differential between the distal side of a phlebotomy needle and a pair of flexible bags or containers. In one of the bags a predetermined quantity of anticoagulant is contained. The other bag serves as a receptacle for the drawn anticoagulated whole blood. A rigid plate is interposed between the two bags. The surface area of opposing surfaces of the bags is made equal to the desired ratio of the anticoagulated whole blood to anticoagulant. These three components, two bags and a plate, are disposed within an air tight chamber having two opposing rigid walls. The bag and components and chamber dimensions are adapted such that the receptacle bag is totally collapsed when the anticoagulant bag is filled and no space is left between the rigid walls, the bags and the plate.

Suitable blood compatible tubing couples the two bags to two branches of a Y-junction, the remaining branch of which is connected to the phlebotomy needle. A hand pump is connected by tubing to the air tight chamber.

The apparatus is then operated after first performing a venipuncture in the donor's arm with the phlebotomy needle. The donor then operates the pump by squeezing the handle of the pump to create a vacuum in the chamber. The surface area of the filled anticoagulant bag is a predetermined fraction of the surface area of the empty receptacle. Therefore, while a vacuum is maintained in the chamber by the continuous operation of the hand pump, anticoagulant will begin to flow from the anticoagulant bag, where it is mixed at the Y-junction with whole blood withdrawn from the donor. The anticoagulated whole blood flows into the receptacle bag. The receptacle bag expands as more and more anticoagulated whole blood flows into the receptacle bag. As the receptacle bag expands it forces the planar plate against the anticoagulant bag. The ratio of the anticoagulant to whole blood is directly related to the ratio of the surface areas of the two bags against the plate. Thus, if a 7:1 mix of whole blood to anticoagulant is desired the surface area of the receptacle bag is made 8 times larger than the anticoagulant bag surface area. Under these conditions a displacement volume of 1 part anticoagulant occurs while at the same time an acceptance volume of 8 parts anticoagulated whole blood occurs in the receptacle bag. The rate at which this occurs is determined by the pressure differential established as the donor operates the hand pump. This rate is therefore literally and figuratively in the hand of the donor.

As may be seen from the above description, a relatively simple apparatus and method is provided which has the following advantageous properties:

the donor has complete control, each flexure of the fist to operate the hand pump creates the driving force for withdrawing blood and coincidentally improves circulation of blood in the donor's hand;

the predetermined ratio of anticoagulant to whole blood is fixed by the ratio of surface bag areas and is independent of tubing dimensions, collection rate, size or length of phlebotomy needle, donor characteristics, height of collection unit with respect to donor, temperature and material characteristics of bag or tubing;

no external power supply is required;

few parts are required in total and specifically very few moving parts are needed;

the tolerance on tubing diameters is non-critical.

BEST MODE OF CARRYING OUT THE INVENTION

A preferred embodiment of this invention can be described in more detail with reference to FIGS. 1-5. The apparatus comprises an anticoagulated whole blood receptacle bag 1 and an anticoagulant supply bag 2 mounted in one rigid vacuum chamber 3 preferably constructed out of a suitable transparent plastic material. The chamber 3 is closed on five sides and has a top plate 6 which opens on the sixth to provide access. The bags 1 and 2 are inserted through the open side, one on either side of a rigid plate 4 whose dimensions are such that it can easily move in either translating direction indicated by arrow A. Top plate 6 is designed to fit into the open side 15 of the rigid vacuum chamber 3. Top plate 6 has a gasket 7 (See FIG. 4) around the mating surface 8. This gasket guarantees a vacuum fit.

Figure 5:
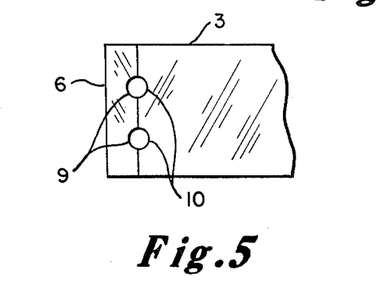
FIG. 5 is a partial end view of the blood chamber with top cover 6 in place.

One side 8 of top plate 6 has two half slots 9 (see FIG. 5). Likewise chamber 3 has opposite half slots 10. These are designed to grip closely the output tube 11 from the anticoagulant bag 2 and the input tube 12 for bag 1. A thin coating of vacuum grease (not shown) on these slots improves the vacuum seal of the chamber 3.

The disposable software package for this invention is simply an anticoagulated whole blood bag 1, an anticoagulant bag 2, and tubes 11 and 12 made out of suitable hemocompatible plastic. The tubes merge at a conventional Y fitment 26 at the hub of a phlebotomy needle 24. The diameter of the phlebotomy needle can be reduced from the conventional 16 gauge if desired, as the system is capable of generating a wide range of vacuum pressures.

The bags 1 and 2 are dimensioned such that the thickness of the anticoagulant bag when full is identical to the thickness of the whole blood bag when full and the ratio of the surface areas of bag 1 to bag 2 at the interface with plate 4 is equal to the desired ratio of anticoagulated whole blood to anticoagulant.

Hand pump 60, which is manually operated by the donor, is coupled via tubing 44 to the interior of chamber 3.

The apparatus of FIG. 1 operates as follows. The site on the donor's arm 22 where the venipuncture is to be made is prepared. A conventional pressure cuff 27 is fastened around the donor's arm 22 at a location above the venipuncture site and sufficient pressure applied to raise the venous pressure enough to boost blood flow from the donor's veins and facilitate venipuncture.

Figure 1:
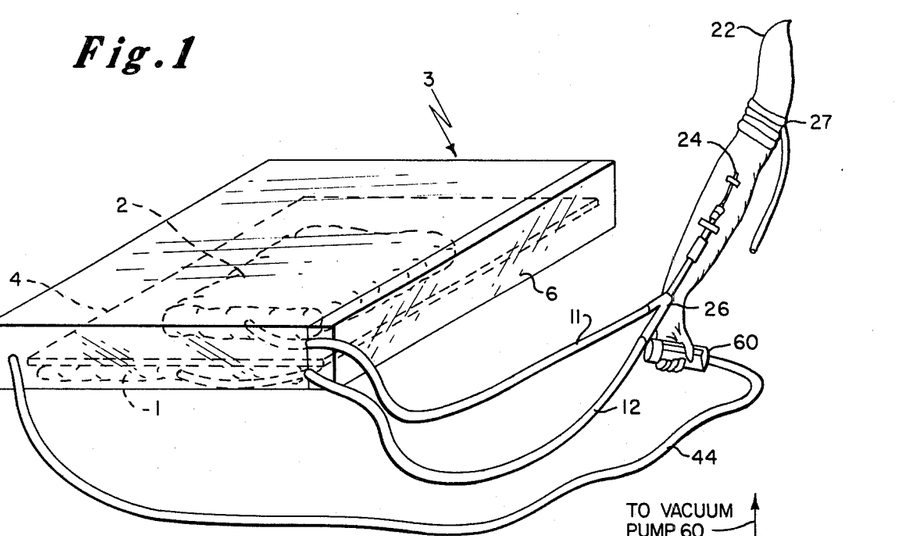
FIG. 1 is a perspective view of the blood donor system connected to a donor's arm.
Figure 2:
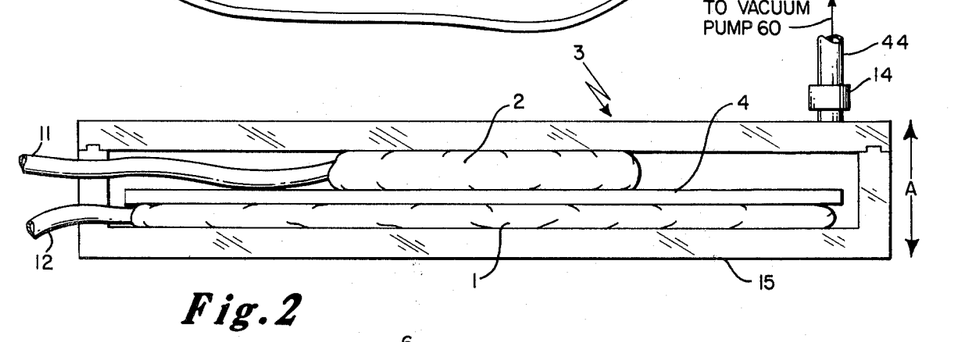
FIG. 2 is an end view of the blood donor chamber with top cover 6 removed.
Figure 3:
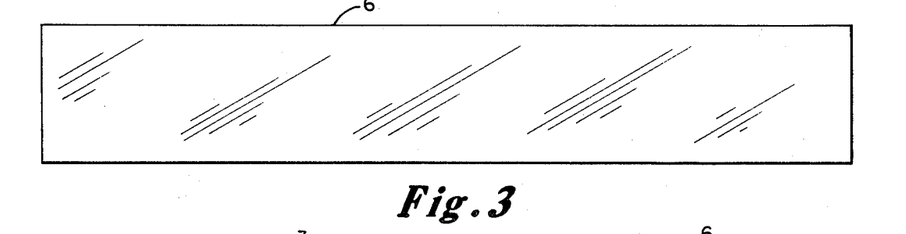
FIG. 3 is an end view of the top cover 6.
Figure 4:
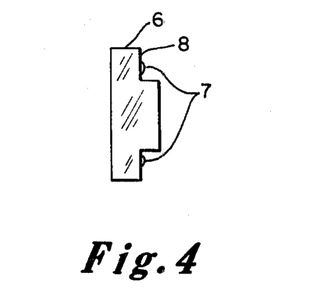
FIG. 4 is a side view of top cover 6.

The apparatus within chamber 3 has already been connected as shown in FIG. 1. Bag 2 is filled with anticoagulant and bag 1 is flat and empty.

A venipuncture is now made and the vacuum pump 60 is manually operating by flexing the donor's fist and moving the pump handle in and out. This produces a vacuum within chamber 3, preferably in the order of 100–400 torr. The vacuum in chamber 3 results in a pressure differential between the bags in the chamber and the distal end of needle 24. Thus, whole blood will be sucked out of the donor's arm at a rate primarily determined by the pressure differential which the donor can maintain by manually pumping. As the whole blood is sucked out it will follow the path of least resistance, which is through conduit 12 to bag 1, and will enter bag 1 expanding the bag against plate 4. As previously mentioned, assuming a 7:1 ratio of whole blood to anticoagulant is desired, bag 1 is dimensioned to have a surface area 8 times the opposing surface area of bag 2. Because of the 8:1 amplification resulting from the ratio of opposing surface areas of bags 1 to bags 2, anticoagulant is expressed out bag 2 when bag 1 expands against plate 4 and plate 4 presses bag 2. The ratio of anticoagulant displaced from bag 2 to anticoagulated whole blood collected in bag 1 as aforesaid, is proportional to the bag surface area ratio at the plate interface. In the specific embodiment described, 1 unit volume of anticoagulant 20 is therefore displaced from bag 2 for each eight (8) unit volumes of anticoagulated whole blood collected in bag 1.

The anticoagulant displaced from bag 2 passes through tubing 11 to Y-junction 26 where it mixes with whole blood and flows to bag 1.

As previously mentioned, the vacuum pressure needed to operate the blood collection system is preferably generated by the flexure of the donor's fist. This is accomplished by operating a hand held vacuum pump 60 such as the pump shown in FIGS. 6-8.

A specific embodiment of a hand pump will be described in connection with FIGS. 6-8, however, any commercially available hand operated pump capable of creating a vacuum pressure in the order of 100–400 torr will suffice. For example, a commercially available hand pump sold by Nalge Company under the designation Nalgene ® hand operated vacuum pump has been employed in an experimental version of the invention.

The pump 60 includes a rocker 31 which is pivotable inside housing 40 on an axle 32. Housing 40 is provided with finger grooves 30 recessed to make it comfortable to hold by the donor. Coil type return springs 38 keep the rocker 31 in compression against the stops 50 on housing 40. Donors are instructed to hold housing 40 in their hands and flex and relax their fist. As the fist is flexed, rocker 31 is pivoted into the housing 40 and the return spring is tensed. As the fist is relaxed, the return spring 38 returns rocker 31 against stops 50, and the return spring is released.

Underneath rocker member 31 is flexible vacuum pouch 33 whose walls are fixed against housing 40 and the inside wall of rocker 31. Thus, when return spring 38 return rocker 31 against stop 50, vacuum pouch 33 must fill with air, through the input-output port 34. This filling air passes through tube 44, twist lock fitment 51, and one way valve 37. Valve 37 prevents any air from traveling through 51 and 44 in the reverse direction. Tube 44 connects to the vacuum chamber 3 housing the anticoagulated whole blood bag 1 and anticoagulant bag 2 previously described.

When rocker member 31 is flexed into housing 40 vacuum pouch 33 is forced to collapse. Air cannot flow through valve 37 and must instead exit through exit valve 35. This one way valve closes by spring action and prevents air from entering on the return stroke.

An adjustable over-vacuum valve 36 is also provided on vacuum pump 60. Valve 36 is closed as long as the vacuum pressure drawn by the hand pump is below a set range determined by the setting of threaded fitment 39. When the vacuum exceeds that range, the ball valve opens and allows air to enter into vacuum pouch 33. An acoustically driven air whistle 41 is fixed on the input to valve 36 so that an audible tone is generated whenever valve 36 opens. Valve 36 is adjusted according to the diameter of phlebotomy needle used, and threaded fitment 39 can be calibrated to be set at various needle gauges depending on the blood collection software used. A smaller diameter phlebotomy needle will require a higher vacuum pressure for the donation, so fitment 39 will be tightened which will put tension on the spring in valve 36 so that it takes a higher vacuum for it to open.

In summary, as the donor's fist is flexed, rocker member 31 compresses vacuum pouch 33 and it empties through valve 35. As the donor's fist is relaxed, rocker 31 expands vacuum pouch 33 and it fills through valve 37, thus taking air from tube 44 and generating a vacuum. The whistle 41 acts to indicate too high a vacuum which means an occlusion in the donor's vein or blood tubing, or that the donation is complete.

An alternate embodiment of the invention which uses positive pressure from a hand pump to operate pressure bags which cause anticoagulant to be displaced and whole blood to be withdrawn will now be described in connection with FIGS. 10 and 11.

Figure 10:
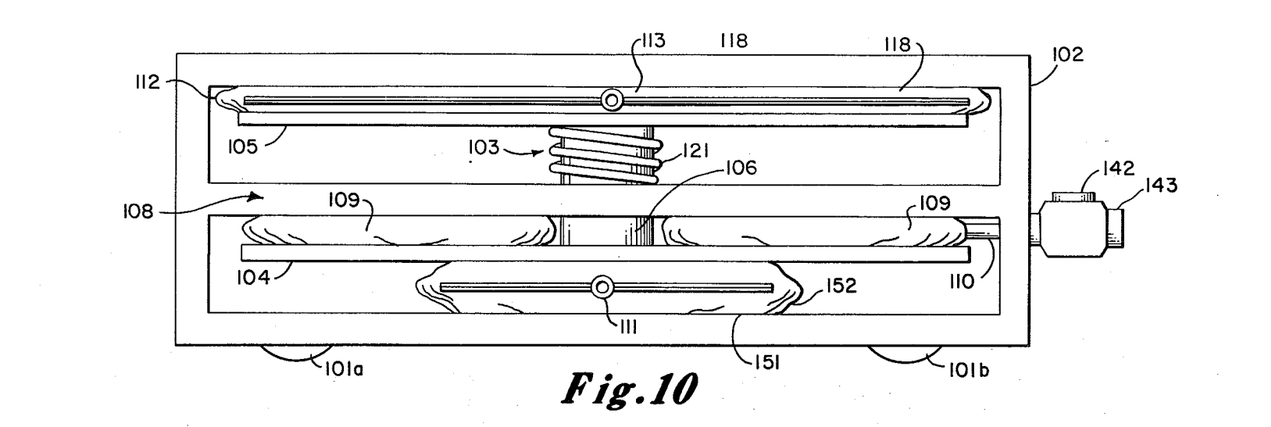
FIG. 10 is an end view of an alternate embodiment of the invention.
Figure 11:
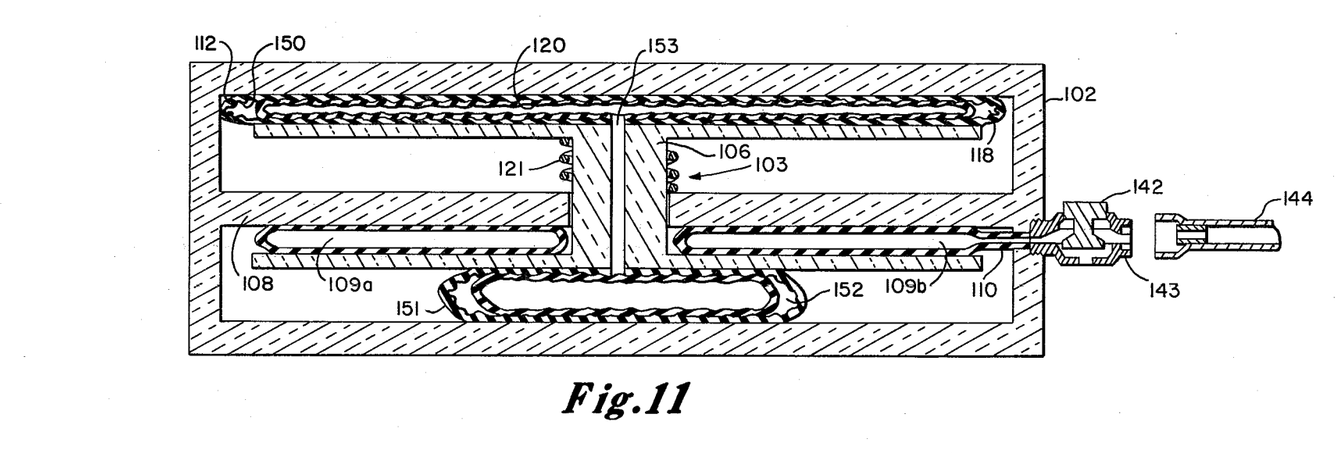
FIG. 11 is a sectional view through the center of FIG. 10.

FIGS. 10 and 11 show a collection platform 102 which is adapted to rest on the floor or on a table next to the donor chair on feet 101(a), and 101(b), as shown in the figure. Collection platform 102 has only one moving part, a piston assembly 103, which is composed of an anticoagulant displacer plate 104, a blood suction plate 105, and three connecting rods 106 with return springs 121 only one of which may be seen in FIGS. 10 and 11. The connecting rods 106 ride in three oversized rod holes 107 in the central septum 108 of the collection platform 102. Between the central septum 108 and the anticoagulant displacer plate 104, two flexible air pressure bags 109a and b, are permanently fixed (one on either side of the connecting rods 106). The input tubes 110 of these bags are connected to a hand operated relief valve 142.

Valve 142 is a three-way valve whose normal state allows flow from tube 144 into the pressure bags 109. When valve 142 is activated by hand it opens the pressure bags 109 to the atmosphere. The output of the valve 142 has a twist lock 143 which connects to a tube 144 which leads to a donor hand pump.

A flexible membrane 112 is permanently connected between the blood suction plate 105 and the collection platform 102. The space inside the flexible membrane 112 defines a vacuum chamber 118 which generates the negative pressure needed to suck the blood from the donor's vein. The inside of membrane 112 may be provided with ribs 150 to help distribute the vacuum over the complete bag surface and prevent sticking. The side of the flexible membrane 113 opens down the middle to allow insertion of an empty blood bag, and removal of a full blood bag.

Figures 6, 7, 8, 9:
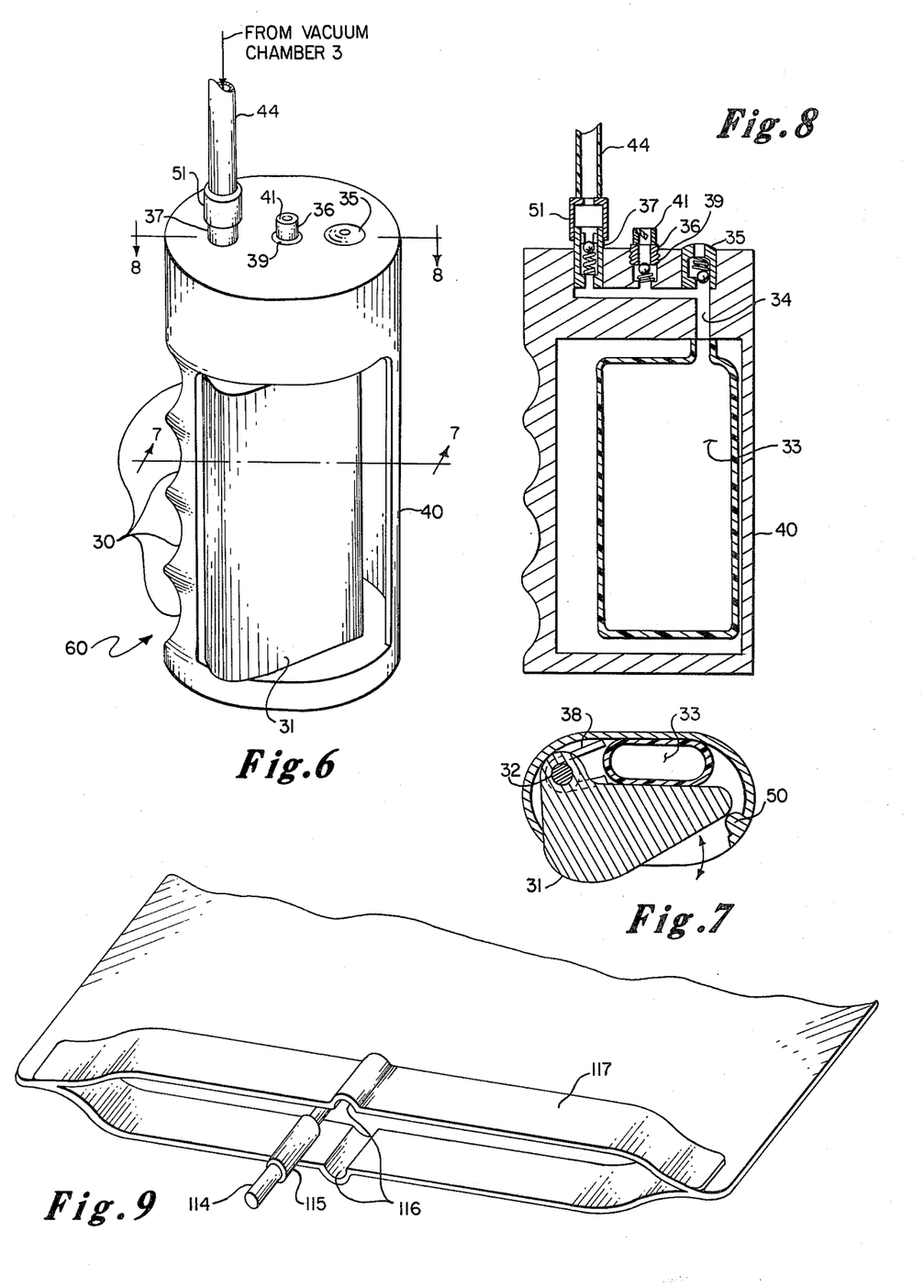
FIG. 6 is a perspective view of a hand vacuum pump for use with the blood donor chamber.
FIG. 7 is a sectional view of the hand pump of FIG. 6, along lines 7—7.
FIG. 8 is a sectional view along lines 8—8 of FIG. 6.
FIG. 9 is a partial perspective view of a bag for use in the embodiment of FIG. 10.

A detail of the flexible membrane opening is shown in FIG. 9. The blood tube 114 has a thickened section 115 which is more rigid than the tube 114 (so it will not collapse under negative pressure) and a more precisely controlled diameter than standard blood tubing (so it will more closely fit into the slot 116 on the flexible membrane). The flexible membrane has a flattened portion or lip 117 about ½" wide, and a slot 116 down the center. The dimension of the thickened section 115 of the blood tube 114 is chosen to fit precisely into the slot 116 to minimize loss of vacuum pressure. A thin coating of stop-cock grease (not shown) aids in forming a good seal of the flexible membrane opening on the blood bag 120 of FIG. 11.

A similar flexible membrane 151 is permanently mounted between the anticoagulant displacement plate 104 and the collection platform 102. This flexible membrane 151 defines a vacuum chamber 152 which holds the anticoagulant bag 111. The vacuum chamber 152 is smaller than the chamber 118 for whole blood—as the anticoagulant bag is only ⅛th the size of the whole blood bag. It has internal ribs 150, and an opening to accept the anticoagulant bag with lip and slot identical to 117 and 116 of chamber 118. Likewise, the anticoagulant tubing has a thickened section at its output identical to 115 of the blood bag. The vacuum chamber 152 seals in the same manner as does chamber 118.

An open port 153 connects vacuum chambers 118 and 152 through one of the connecting rods 106. Thus, the pressure in chambers 152 and 118 is identical.

The dimensions of the anticoagulant bag 111 to be held in chamber 152 and of the whole blood bag 120 to be held in chamber 118 are chosen so that the height H of the anticoagulant bag 111 when full (i.e., 63.5 ml anticoagulant) is equal to the height when the whole blood bag 120 is full (i.e., 450 ml whole blood + 63.5. ml CPD anticoagulant). Thus, the projected surface area of the anticoagulated whole blood bag (width times length) is 8 times that of the anticoagulant bag. This guarantees a fixed ratio of anticoagulant to anticoagulated whole blood. Any motion of the piston 103 causes the displacement volume of 1 part anticoagulant and the acceptance volume of 8 parts anticoagulated whole blood.

The operation of the collection platform is as follows. In order to facilitate loading of the platform, the hand operated relief valve 142 is closed and the flexible air pressure bags 109 are filled, bringing the piston 103 to the bottom and maximizing the open space in the vacuum chamber 118. The two lips 117 of the flexible membrane opening 113 are spread apart and an empty blood bag 120 is placed inside the vacuum chamber 118. The relief valve 142 is then opened and the pressure bags 109 emptied by the force in the return springs 121 bringing the piston 103 to the top and removing most of the air from the chamber 118. The lips 117 of the membrane opening 113 are then pressed together and sealed. The vacuum chamber 152 on the anticoagulant side is then opened in a manner similar to chamber 118, and a full anticoagulant bag is placed inside chamber 152. Chamber 152 is then pressed together and sealed. The hand operated relief valve 142 is then closed.

As in the apparatus of FIG. 1, tubing (not shown) from the anticoagulant bag 111 joins the tubing leading to the anticoagulated whole blood bag 120 just downstream of the phlebotomy needle (not shown) with a conventional Y fitment (not shown).

As air is slowly pumped into tube 144 from a hand pump (to be described) and into pressure bags 119, piston 103 is forced to move generating a vacuum in chamber 118 and in 152 and also displacing anticoagulant from the anticoagulant bag 111.

The pressure needed to move the piston 103 in the collection platform 102 is preferably generated by the opening and closing motion of the donor's fist. It can be shown that 280 torr of pressure is needed to get 60 ml/min. flow rate of whole blood through a 19 gauge thin wall phlebotomy needle. This magnitude of vacuum can easily be generated by closing one's fist about a pressure bulb. Such an action also aids the blood collection, as it will increase flow from capillary to vein in the donor's arm.

Figure 12:
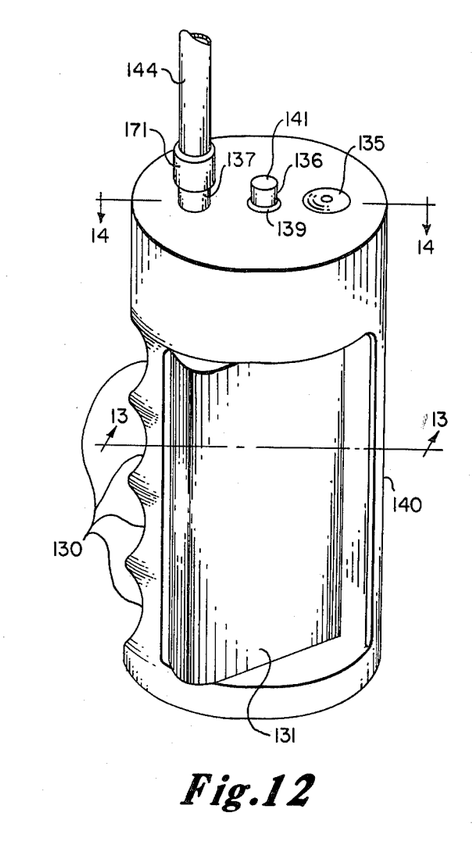
FIG. 12 is a perspective view of a hand pressure pump for use with the apparatus of FIG. 10.
Figure 13:
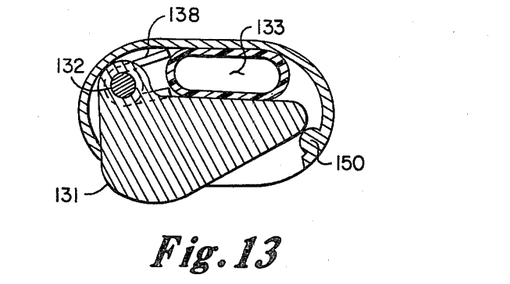
FIG. 13 is a sectional view of the apparatus of FIG. 12 taken along lines 13—13.
Figure 14:
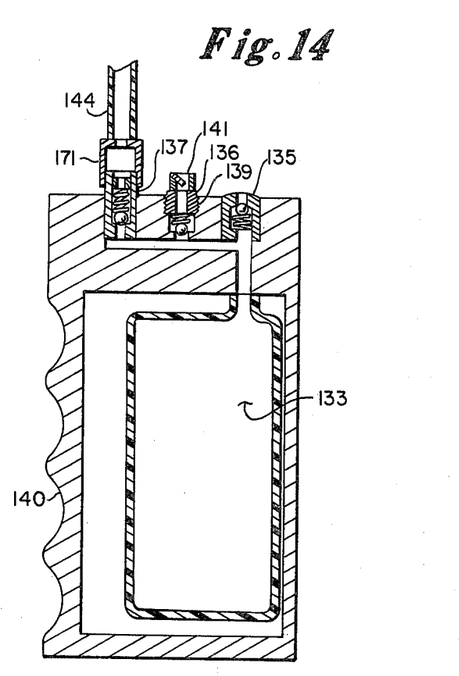
FIG. 14 is a sectional view along lines 14—14 of FIG. 13.

The pump in FIGS. 12–14 is adapted to be held in the donor's fist and is similar to the vacuum pump previously described but here it has been modified to provide positive air pressure. Recessed finger grooves 130 are provided to make the pump fit comfortably in the fist. Pump pressure is generated by the inward rocking motion of the finger rocker member 131 which rides on the pivot axle 132. Return springs 138 forces the finger rocker 131 to open and the pressure pouch 133 to refill when the fist is relaxed. Immediately beneath the finger rocker 131 is a pressure pouch 133 whose walls are fixed to the inner wall of the finger rocker 131 and the inner wall of the hand pump. This pouch can be constructed of any flexible polymer material. The volume of the pouch is so designed to provide a limit of the pressure stroke to less than 3 to 5 cc of air so as to limit the blood flow to no more than 3 to 5 ml per fist flex. The output tube of the pressure pouch 134 leads to an input check valve 135, a pressure relief valve 136, and an output check valve 137, before it terminates at a twist lock fitment 171. The valves 135, 136 and 137 are similar to those previously described and are conventional and commercially available. They are arranged so that air can enter the pressure pouch only through valve 135 and leave only through valve 137. The input diameter of the check valve 135 is made small enough to impose a dwell time to refill the pressure pouch 133 and to recoil the finger rocker 131. This dwell time will give sufficient time for the 3 to 5 ml of anticoagulant whole blood to flow into the collection bag and not allow over-work of the donor's fist. Valve 131 has an air powered whistle 141 attached at its output. Any air leaked through 136 will cause an audible signal which will serve as a warning as described below.

Pressure relief valve 136 is adjustable (by turning the threaded fitment 139) and can be set for a particular phlebotomy needle design as described in connection with vacuum pump 60.

In operation, the pressure regulated hand pump 140 is attached to the collection platform 102 with a conventional flexible air hose 144 with a twist lock 171. The blood collection software is mounted into the collection platform as described above. The phlebotomy is then made and the donor is given the hand pump (which can be turned upside down for righthand donors) and instructed to flex and relax his or her fist, as is currently the practice. Each time the fist is flexed some predetermined volume of air is pumped from the pressure pouch 133 in the hand pump into the flexible air pressure bag 109. This will force the piston to move and to create a vacuum in the vacuum chambers 118 and 152 and inside the blood bag 120 and a displacement pressure in the anticoagulant bag 111. This results in the flow of anticoagulant into the needle fitment, and flow of blood from the donor's arm.

Each time the donor's fist is flexed, another volume of air from the hand pump pumps a ratioed volume of anticoagulant from the anticoagulant bag and sucks a ratioed volume of blood from the vein. The donor is in complete control. If an occlusion occurs some place in the system, the pressure relief valve 136 in the hand pump will open when the pressure in the pressure pouch-flexible pressure bag becomes greater than a pre-set limit. The pressurized air from the pressure pouch will then pass through the relief valve 136 and through the whistle 141. This will generate a warning tone for the nurse to hear. It will indicate that something is wrong with the system, a kink in the tube or that the phlebotomy needle is up against the wall of the donor's vein and has to be repositioned. At the end of the collection, the piston 103 will bottom out on the collection platform. Subsequent flexures of the donor's fist will generate pressures in excess of the pre-set pressure of the relief valve. Here too, the whistle 141 will sound upon each flexure and indicate that the nurse should return to the scene.

Figure 15:
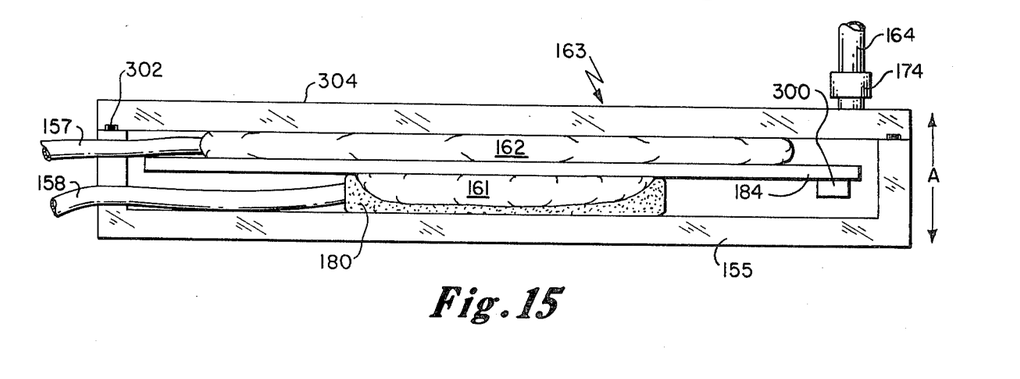
FIG. 15 is an end view of a further embodiment of the invention.

An alternate embodiment of the invention is shown in FIG. 15. The construction of the chamber 163 is similar to that employed in FIG. 2 so a detailed description is not required here. Suffice it to say that the chamber is constructed of plastic walls 155 provided with air tight openings to permit entry of tubes 157, 158 and 164. Top wall 304 is provided with a gasket 302 about its periphery to enhance its air tight fit with the side walls. Tube 164 is connected at one end to a hand operated vacuum pump (not shown) and at the other through valve 174 to the interior of vacuum chamber 163. Anticoagulated whole blood bag 162 is disposed within chamber 163 on planar plate 184 and rests on soft spongy cradle 180 molded to form a good fit about anticoagulant bag 161 which has a cross-sectional crescent shape; but is otherwise identical to the previously described bags. As in FIG. 1, blood-compatible tubing 157 and 158 connect respective bags 162 and 161 to a Y-junction at the hub of a phlebotomy needle (not shown). A stop mechanism 300 is mounted on plate 184. The function of this stop will be described in detail below.

It may thus be seen that except for the cradle 180 and the shape of bag 161 and the addition of stop 300, the embodiment of FIG. 15 is identical to that of FIGS. 1–4.

Stop 300 may comprise a block of rigid material such as wood, metal or plastic, removably disposed on plate 184 as shown in FIG. 15. The height of the block determines the total lateral upward displacement of plate 184 and therefore the number of units of anticoagulated whole blood units withdrawn. Bag 162 fills as bag 161 empties until stop 300 restrains plate 184 from further motion. Various sizes of stops 300 can be made for various collection volumes. Such a capability may be of importance, for example, in pediatric blood donations.

The function of the non-uniform cross-sectional dimension of bag 161 is to provide a variable ratio of anticoagulant to whole blood collection during the course of the donation procedure. This is achieved in FIG. 15 by charging the cross-sectional shape of the anticoagulant bag from a rectangular parallelepiped to a crescent shape, for example. In the rectangular bags of previous embodiments, the volume is equal to the thickness times the cross-sectional area; hence, constant volumes of anticoagulant are expressed for equal changes in thickness, inasmuch as the cross-sectional area of the bags remains substantially constant during the procedure.

However, with a bag 161 of crescent cross-sectional shape as shown in FIG. 15, supported in a spongy cradle 180, varying volumes of anticoagulant will be displaced from bag 161 for each unit of displacement.

It should be noted that the final ratio of whole blood to anticoagulant would always be the same in such a device, but that the instantaneous ratio of whole blood mixing with anticoagulant at the needle site at any time is variable. This might be advantageous if one wanted to mix, for example, equal parts of anticoagulant to whole blood at the very beginning of a donation procedure, while still ending up with a final ratio of 7:1 whole blood to anticoagulant.

In the embodiments previously described, the ratio of anticoagulant to whole blood is maintained throughout the collection at some value determined by the geometries of a flexible anticoagulated blood receiver bag and flexible anticoagulant bag. The anticoagulant bag must be flexible, as it is emptied by the motion of a rigid plate which is driven by the filling of the anticoagulated whole blood receiver bag. Because of problems associated with the manufacture and sterilization of flexible bags, in some applications it may be desirable to manufacture the anticoagulant in a glass bottle. The embodiment of FIG. 16 represents a version of the invention which incorporates such a rigid glass anticoagulant container.

Figure 16:
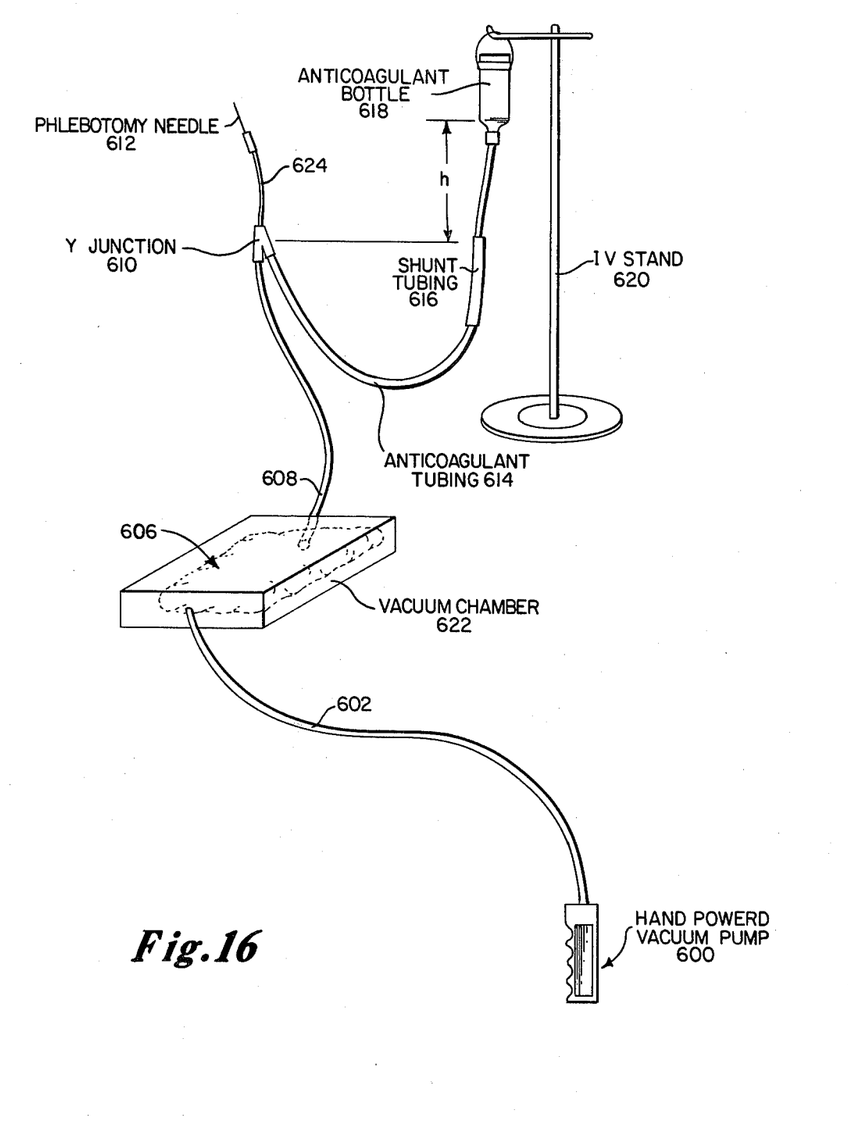
FIG. 16 is a diagrammatic representation of an anticoagulant gravity feed embodiment of the invention.

In the apparatus of FIG. 16, the vacuum chamber 622 of previous embodiments has been altered to accept an anticoagulated whole blood bag 606 only. The rigid barrier and the anticoagulant bag of previous embodiments are no longer within the vacuum chamber. Instead, the anticoagulant is contained in a rigid glass vial or bottle 618 which can be held on a short I.V. stand 620 for observation. The anticoagulant tubing 614 joins the blood tubing 624 just downstream of the phlebotomy needle 612 at one side of Y-junction 610. The other side of Y-junction 610 is connected to anticoagulated whole blood bag 606 via tubing 608. A hand powered vacuum pump 600 such as previously described, is coupled via tubing 602 to the inside of vacuum chamber 622. The anticoagulant tubing 614 includes a section of shunt tubing 616 which limits the rate of flow of anticoagulant from the anticoagulant bottle 618.

The height of the anticoagulant bottle 608, h, and the inside diameter and length of the shunt tubing 616 are dimensioned so that with a pre-set vacuum pressure in the vacuum chamber, the anticoagulant bottle will empty completely in a time equal to $T_{min}$. $T_{min}$ is the shortest time it takes to collect a full unit of anticoagulated whole blood with a given vacuum chamber, anticoagulated whole blood bag and hand pump. This time may be established by empirical measurement of a representative donor sample. For the experimental unit we employed, $T_{min}$ was 4 minutes for a vacuum chamber and bag which accepted 450 ml of whole blood mixed with 63.5 ml of anticoagulant. While the anticoagulant to whole blood ratio is high during the first 4 minutes of the donation, it will come down to the desired level at the end of the collection. Anticoagulant shock, a phenomena which occurs with prior art donation methods, is avoided because the mixture of anticoagulant with the whole blood is spread out over the first 4 minutes. Also, mixing of the blood bag during collection—a requirement in the prior art methods—is not required as the blood and anticoagulant will be adequately mixed at the Y-junction 610.

It should be noted that the section of shunt tubing 616 could be replaced by an orifice, clamp or other flow restricting device to achieve the same result.

Equivalents

Those skilled in the art will recognize many equivalents to the specific embodiments described herein. Such equivalents are part of this invention and are intended to be covered by the following claims. For example, the tubing from the anticoagulant bag could be made to intersect with the whole blood tube within chamber 3 of FIG. 1 rather than at the phlebotomy needle 24 in which case only one slot 9 would be required for the whole blood line 1. The blood and anticoagulant would then mix inside the chamber before entering the bag. It should also now be clear that because of the blood flow assist generated by the pumping action, the apparatus of the invention is capable of collecting blood with 19 or 20 gauge phlebotomy needles instead of the larger 16 gauge needles currently in use.

It should also be noted that the embodiments of FIGS. 1-8 and 9-14 are equivalent in many respects. The two vacuum chambers 152 and 118 of FIG. 11 are at the same pressure level by virtue of conduit 153 and hence may be considered equivalent to the single vacuum chamber 3 of FIG. 1. The piston mechanism 103 of FIG. 11 is a way of converting the positive pressure from the hand pump of FIGS. 12-14 to create a negative pressure or vacuum in the chambers. In the apparatus of FIGS 1-8 the vacuum pressure is created directly by means of the hand held vacuum pump 60.

We claim:

1. A blood collection apparatus comprising:
   (a) a first flexible bag for receiving a first fluid which is a mixture of a second and third fluid;
   (b) a second flexible bag containing said second fluid to be mixed with said third fluid in accordance with a predetermined ratio;
   (c) a rigid member interposed between said first and second bags;
   (d) an airtight chamber enclosing said bags and member;
   (e) conduit means for coupling said first and second bags to respective first and second ports of a three-port junction, the third port of said junction being coupled to the proximal end of a phlebotomy needle;
   (f) pump means for causing a pressure differential between said first bag and the distal end of said phlebotomy needle whereby when the distal end of said phlebotomy needle is coupled to a source of third fluid, said first bag is caused to begin to fill with fluid and displace the rigid member which causes the second fluid in the second bag to begin emptying and flowing to said junction where it mixes with the third fluid and passes to the first bag.

2. The apparatus of claim 1 wherein said pressure differential is caused by pumping air out of said chamber.

3. The apparatus of claim 1 wherein said pressure differential is caused by pumping air into an air bag bag adjacent said chamber which upon expanding causes a vacuum in said chamber and moves said rigid member toward said second bag and away from said first bag.

4. The apparatus of claim 1 in which the ratio of
   (i) the surface area of the first bag adjacent and normal to said rigid member to
   (ii) the surface area of the second bag adjacent and normal to said rigid member:
is directly proportional to the predetermined ratio of mixing of fluids, and the thickness "t" of one bag when full is substantially equal to the thickness of the other bag when full wherein "t" is the maximum allowable expanded internal width of a bag when full of fluid and confined in said chamber.

5. The apparatus of claim 1 in which the ratio of
   (a) a first flexible bag for receiving a first fluid which is a mixture of a second and third fluid;
   (b) a second flexible bag containing said second fluid to be mixed with said third fluid in accordance with a predetermined ratio;
   (c) a rigid member interposed between said first and second bags;
   (d) an airtight chamber enclosing said bags and member;
   (e) conduit means for coupling said first and second bags to respective first and second ports of a three-port junction, the third port of said junction being coupled to the proximal end of a phlebotomy needle;
   (f) pump means for causing a pressure differential between said first bag and the distal end of said phlebotomy needle whereby when the distal end of said phlebotomy needle is coupled to a source of third fluid, said first bag is caused to begin to fill with fluid and displace the rigid member which causes the second fluid in the second bag to begin emptying and flowing to said junction where it mixes with the third fluid and passes to the first bag.

6. The apparatus of claim 5 in which the pump means is manually operable.

7. The apparatus of claim 1 in which the cross-sectional internal dimension between sides of one of the bags in a direction normal to the rigid member is uniform.

8. The apparatus of claim 1 in which the cross-sectional thickness of one of said bags is non-uniform.

9. The apparatus of claim 1 in which a stop means is provided between the rigid member and a wall of said chamber.

10. The apparatus of claim 1 wherein the airtight chamber has two opposing rigid walls, the rigid member and first and second bags are disposed adjacent to such walls and the quantity of second fluid in said second bag is sufficient to fill the second bag and the first and second bag and internal chamber dimensions are such that when a vacuum is established in the chamber and the first bag is thereby totally collapsed no space is left between the adjacent walls, the collapsed first bag and the filled second bag and the member.

11. The apparatus of claim 1 in which the thickness "t" of one bag when full is substantially equal to the thickness of the other bag when full, and wherein "t" is the maximum allowable expanded internal width of a bag when full of fluid and confined in said chamber.

12. The apparatus of claim 1 in which the first fluid is anticoagulated whole blood, the second fluid is anticoagulant, and the third fluid is whole blood from a donor.

13. The apparatus of claim 1 in which the pump means is manually operable.

14. A blood donor system comprising in combination:
(a) a phlebotomy needle;
(b) a first conduit adapted to be connected at one end to a source of anticoagulant in an anticoagulant bag and at the other end to said phlebotomy needle;
(c) a second conduit adapted to be connected at one end to a collection bag and at the other end to said phlebotomy needle and said first conduit;
(d) hand held pump means creating a negative pressure differential between the distal end of the phlebotomy needle and the collection bag to cause blood from a donor to flow through said phlebotomy needle to said collection bag;
(e) the anticoagulant bag and collection bag being disposed in a rigid chamber with a pressure plate intermediate the two bags forming an inter-face there between.

15. The apparatus of claim 14 in which signal means are provided in association with said pump means to indicate when the pressure differential exceeds a predetermined pressure level.

16. The apparatus of claim 15 in which a volume of blood is to be collected in the collection bag and the ratio of the surface area of the anticoagulant bag and collection bag at the interface with the pressure plate is directly proportional to the desired mixture of anticoagulated whole blood to anticoagulant.

17. A blood donor collection apparatus comprising in combination:
(a) a first conduit;
(b) a second conduit;
(c) a flexible bag means for containing anticoagulated whole blood connected to one end of the second conduit;
(d) a flexible bag means for containing anticoagulant connected to one end of the first conduit;
(e) the remaining ends of said first and second conduits being coupled to opposite branches of a three-port device, the remaining branch of which is coupled to a phlebotomy needle;
(f) the ratio of the surface areas of at least one pair of adjacent surfaces of said bag means being directly proportional to the ratio of the volume of anticoagulated whole blood to be collected and the volume of anticoagulant to be mixed with the whole blood.

18. The apparatus of claim 17 in which the thickness "t" of the collection bag when full is equal to the thickness of the source bag when full and wherein "t" is the expanded internal width of a bag when filled with fluid.

19. The apparatus of claim 17 including a vacuum chamber in which the apparatus of (a)-(d) are disposed with said first and second conduits extending from said chamber.

20. The apparatus of claim 16 including a vacuum pump connected to said chamber.

21. A blood donor system comprising:
(a) a phlebotomy needle for making a venipuncture in a donor's arm;
(b) an initially empty blood collection bag means;
(c) an anticoagulant bag means for storing anticoagulant which is initially substantially filled with anticoagulant;
(d) conduit means interconnecting each of said bag means and said needle;
(e) each of said bag means being substantially thin elongate planar plastic structures;
(f) hand operated pump means for causing said anticoagulant to be mixed with blood from the donor in a predetermined ratio established by the ratio of the planar surface area of said bags in the direction normal to each other when oppositely disposed and independent of the amount of blood withdrawn from the donor.

22. The apparatus of claim 21, including means on said pump to indicate when the pressure in the pump means has exceeded a predetermined range.

* * * * *